United States Patent [19]
Umemura et al.

[11] Patent Number: 4,865,042
[45] Date of Patent: Sep. 12, 1989

[54] ULTRASONIC IRRADIATION SYSTEM

[75] Inventors: Shin-ichiro Umemura, Hachioji, Japan; Charles A. Cain, Urbana, Ill.; Kageyoshi Katakura, Meguro, Japan

[73] Assignee: Hitachi, Ltd., Tokyo, Japan

[21] Appl. No.: 894,843

[22] Filed: Aug. 8, 1986

[30] Foreign Application Priority Data

Aug. 16, 1985 [JP] Japan ................................. 60-179420
Oct. 14, 1985 [JP] Japan ................................. 60-226716
Oct. 14, 1985 [JP] Japan ................................. 60-226717

[51] Int. Cl.[4] .............................................. A61B 6/00
[52] U.S. Cl. ................................ 128/660.03; 128/804; 310/334; 310/335
[58] Field of Search .................. 128/660, 24 A, 303.1, 128/362, 399, 401, 804; 310/334–337, 367, 369; 73/626, 602

[56] References Cited

U.S. PATENT DOCUMENTS 4,324,140 4/1982 Auld .
4,327,738 5/1982 Green et al. .................. 128/660
4,398,422 8/1983 Haerten ....................... 128/660 X
4,441,486 4/1984 Pounds .
4,586,512 5/1986 Do-Huu et al. .................. 128/660

FOREIGN PATENT DOCUMENTS 2418472 10/1979 France ............................... 128/660
2113099 8/1983 United Kingdom .
2126901 4/1984 United Kingdom .

OTHER PUBLICATIONS

"An Annular Focus Ultrasonic Lens for Local Hyperthermia Treatment of Small Tumors", by Ralph E. Beard et al., 1982, pp. 177–184.
1981 Ultrasonics Symposium Proceedings, B. R. McAvoy, Editor, pp. 632–637.

Primary Examiner—Ruth S. Smith
Attorney, Agent, or Firm—Antonelli, Terry & Wands

[57] ABSTRACT

Herein disclosed is a system for irradiating sound waves to be converged into an annular focal zone having a desired size. This system uses a transducer which is composed of a plurality of elements divided at least in a circumferential direction of the face of the transducer so that the phases of drive signals may be changed according to the respective circumferential positions of the oscillating elements to rotate the phases of the drive signals n rotations in the circumferential direction. As a result, the annular focal zone of having a desired radius is formed, and integrated values of sound waves in the circumferential direction may be substantially zero on the focal plane so that an unnecessary secondary focal zone is prevented from being formed.

8 Claims, 12 Drawing Sheets

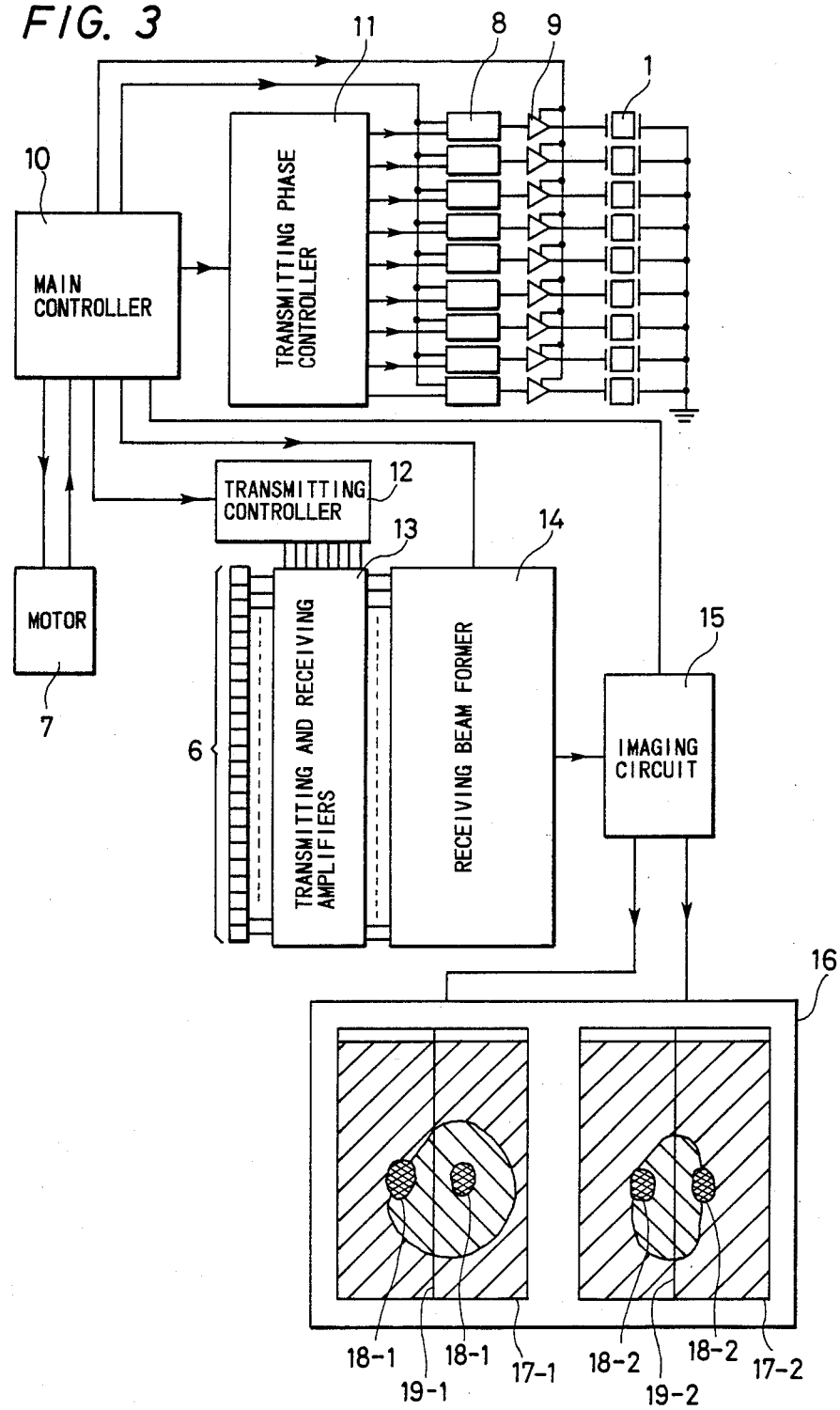

n=4

Z = 80mm = $Z_F$ n=8

Z = 80mm = $Z_F$

ULTRASONIC IRRADIATION SYSTEM

BACKGROUND OF THE INVENTION

The present invention relates to an ultrasonic irradiation system such as an ultrasonic heater, an ultrasonic chemical reaction accelerator or a sonicator and, more particularly, to an ultrasound therapy system suitable for therapy of malignant tumors.

In each application field of the ultrasonic irradiation including a medical treatment, an ultrasound focal zone of single spot focus may be too small, as compared with a target zone to be irradiated. As an ultrasonic irradiation system suited for this application, there has been known in the art a system for forming an annular focal zone by using such an acoustic lens as is disclosed in "Ultrasound in Med. & Biol." vol. 8, No. 2 (issued in 1982), pp. 177 to 184. However, this system is encountered with an inconvenience that the position, size and shape of irradiation cannot be controlled in accordance with an object to be irradiated with ultrasonic waves because they are fixed. Moreover, the system has a tendency that the ultrasonic waves spreading again from an annular focal zone A will reform a long column-shaped focal zone B on the center axis of the annulus, as shown in section in FIG. 1. This tendency is strengthened to raise a serious problem especially in case the diameter of the annulus is smaller than that of the ultrasonic probe. In the field of ultrasound therapy, for example, the secondary focal zone other than the target zone to be irradiated may adversely affect the normal internal tissues of a patient or may cause pain in him.

SUMMARY OF THE INVENTION

An object of the present invention is to provide an ultrasonic irradiation system capable of forming a larger focal zone than the single spot focus and making its area variable.

Another object of the present invention is to provide an ultrasonic irradiation system for forming a larger focal zone than the single spot focus without any secondary focal zone other than the target zone.

According to a feature of the present invention, an annular or elliptic focal zone is formed on certain focal plane by means of a transducer having an array of transducer elements arranged so that the integrated value of sound pressure on the focal plane may always be so small as can be substantially neglected, as compared with the integration of the absolute sound pressure generated by the transduce elements.

More specifically, sound waves are so generated along an annular focal zone that the phase of their sound pressures may rotate in the circumferential direction. For this purpose, by using a transducer having a two-dimensional array of separate transducer elements in each circular path, the phases of signals for driving the respective separate elements in a circular path are rotated around the center of the transducer in the circumferential direction so that the phase distribution rotates through 360 electrical degrees for the circumference of the circular path. For forming the focal zone, on the other hand the phases of the drive signals of the respective elements are also modified according to the position in the radial direction. The focal distance can be varied by adjusting the phases of the driving signals in the radial direction.

Incidentally, the adjustment of the phases of the drive signals in the radial direction is unnecessary if the original phase of the drive signals is sufficient to fix the focal distance. Therefore, this focal zone can be formed either by using an acoustic lens or by making the transducer face concave. In this case, the transducer may be of radial array type in which a transducer plate with a circular or a similar shape is divided into a plurality of elements along the circle.

In order to control the size of the focal zone, on the other hand, the number of poles $2n$ ($n=1, 2, 3, 4$ and so on) of the drive signals is changed. The diameter of the annular focal zone is enlarged by increasing the number $2n$ of the poles.

BRIEF DESCRIPTION OF THE DRAWINGS

FIG. 3 is a block diagram showing one embodiment of the present invention;

DESCRIPTION OF THE PREFERRED EMBODIMENTS

Figure 2:
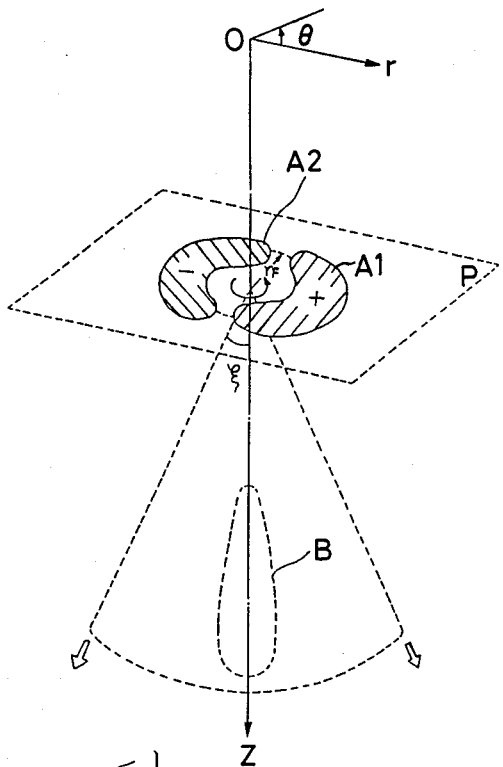
FIG. 2 is a schematic diagram showing a focal zone according to the present invention.

FIG. 2 shows the situation of a sound field formed by a representative embodiment of the present invention.

If the phase of the sound pressure of an annular focal zone on a focal plane P is intentionally modulated along the annulus so that the integration of sound pressure on P may substantially equal to zero, an acoustic energy necessary for forming annular focal zones A1 and A2 on the focal plane P can be concentrated without forming any secondary focal point B. In other words, the focal zones formed on the focal plane P are asymmetric with respect to the center axis so that the sound pressure on the axis is always kept to be zero.

If, moreover, the point where the phase of the sound pressure is zero is rotated, as indicated by thick arrows in FIG. 2, the acoustic energy time-averaged averaged on the annulus can be shaped to form the desired acoustic energy irradiation pattern.

The present invention will be described more in detail in the following in connection with the embodiments thereof. FIG. 3 is a block diagram showing an ultrasonic irradiation system according to one embodiment of the present invention, and FIGS. 4A and 4B, FIGS. 6A and 6B, and FIGS. 8A and 8B are top plan views and sectional views showing three examples of an ultrasonic probe being a part of the ultrasonic irradiation system, respectively.

Figure 4A:
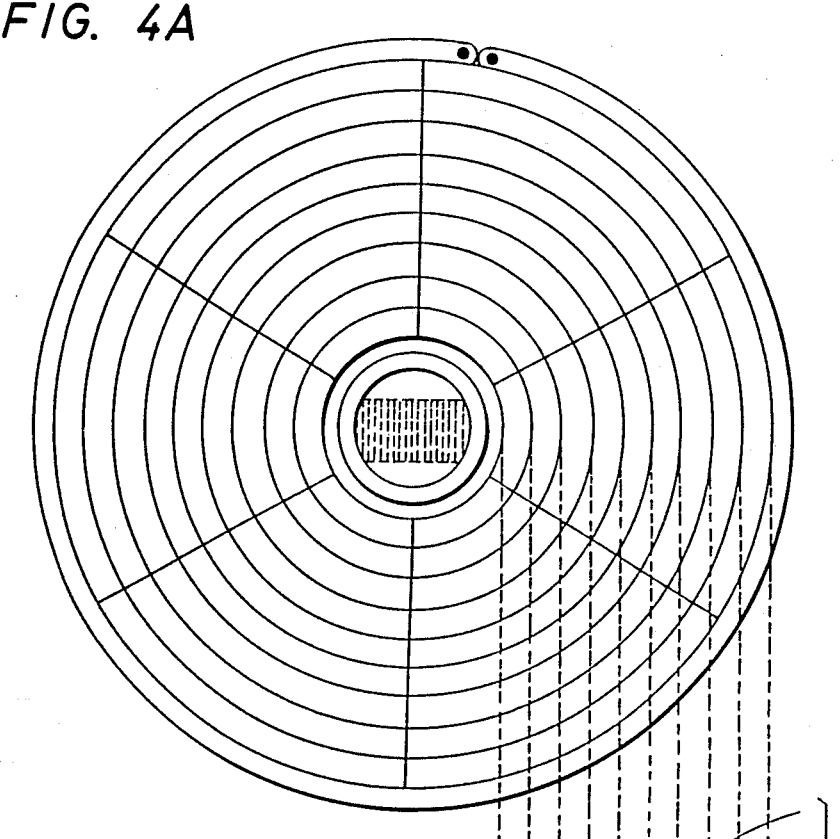
FIGS. 4A and 4B, FIGS. 6A and 6B, and FIGS. 8A and 8B are top plan views and sectional views showing respective examples of the probe.
Figure 4B:
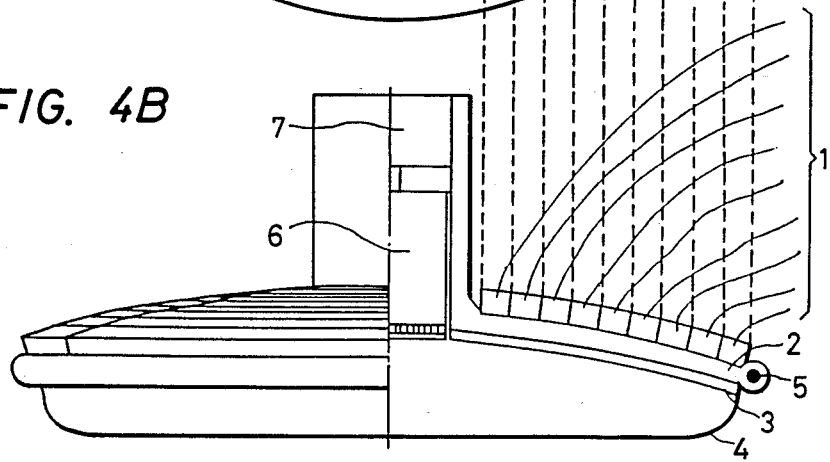
Figure 6A:
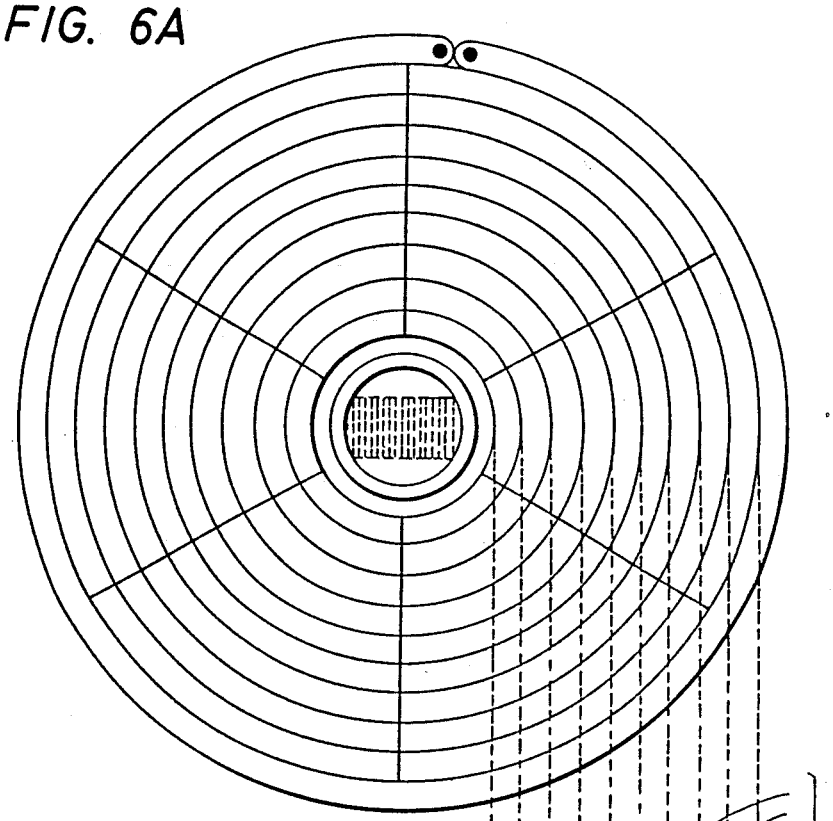
Figure 6B:
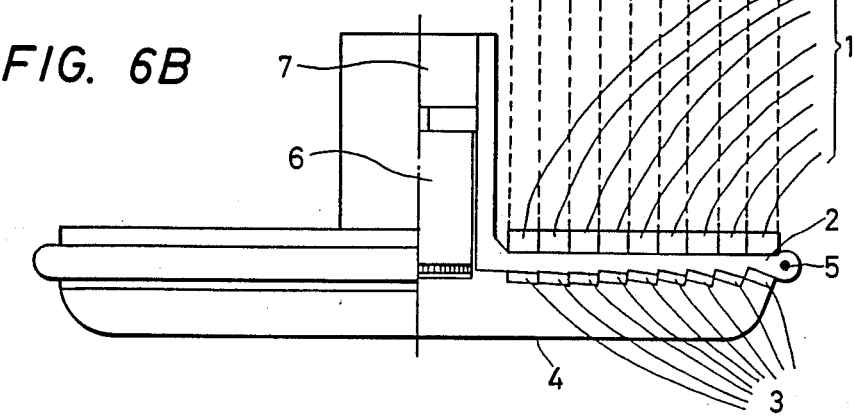
Figure 8A:
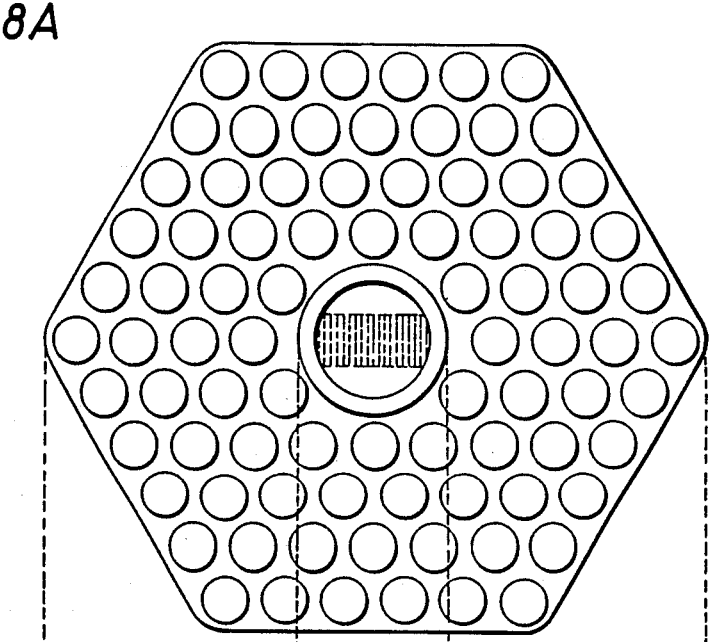
Figure 8B:
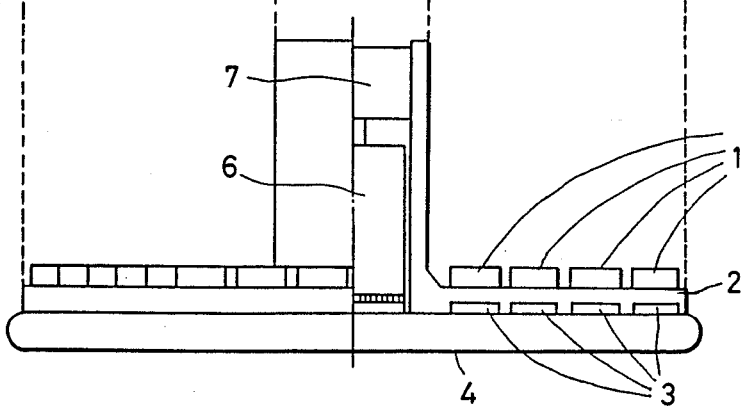

First of all, the constructions of the probes shown in FIGS. 4A and 4B, FIGS. 6A and 6B, and FIGS. 8A and 8B will be described in the following. In any of the examples of the probe, transducer 1 made of piezoelectric ceramics and a second acoustic matching layer 3 made of a polymer are adhered to the front and back sides respectively of a board 2 of light metal which serves as a first coustic matching layer, as a ground eletrode and as a heat sink, respectively. A water bag 4 for acoustic coupling between the transducer and an object to be irradiated is attached to the second acoustic matching layer 3. In the example of FIGS. 4 and 6, the transducer 1 is divided into concentric ring-shaped transducer elements, nine being illustrated, each of which is radially divided into six transcuer elements. A total of 54 transducer elements may thus be provided. In the example of FIG. 8, on the other hand, the transducer is constructed by arraying a plurality of escillating elements regularly two-dimensionally. Thus, the transducer for irradiating sound waves to an annular focal zone is constructed of those plural transducer elements. In any of the examples of FIGS. 4, 6 and 8, on the other hand, an auxiliary probe 6 for monitoring the irradiation is rotatably fitted in the central portion of the probe. That auxiliary probe 6 is of a small linear (or convex) array type, in which the transducer elements have a resonance frequency between 100 KHz and 10 MHz, which is selected to be two or more times as high as the resonance frequency of the transducer 1. In a suitable example, the transducer 1 has a resonance frequency of 500 kHz whereas the auxiliary probe 6 has a resonance frequency of 3 MHz. The orientation of the array of the auxiliary probe 6 is rotationally controlled by means of a motor 7.

A cooling pipe 5 is fitted in the light metal board 2 of FIGS. 4 and 6. In the example of FIG. 8, on the contrary, the cooling pipe can be dispensed with because the light metal board 2 is constructed to touch directly with the acoustic coupling water confined in the water bag 4.

Figure 5:
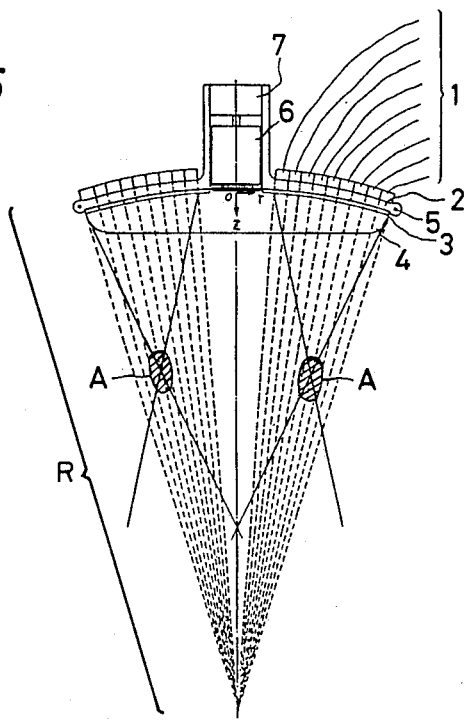
FIG. 5 is a schematic diagram showing the focal zone formed by the probe of FIGS. 4A and 4B.

In the embodiment of FIG. 4, as shown in section in FIG. 5, the probe is given a finite curvature R so as to allow a reduction in the number of the transducer elements necessary for scanning the target zone by changing the radius and depth of the annular focal zone A. By thus setting the maximum direction of the directivity of transducer outer elements inward, the number of the elements required can be reduced to about one half of the number required for a planar probe. A similar effect can also be attained by combining a planar oscillator and an acoustic lens. This combination is exemplified by the example of FIG. 6, in which the acoustic lens is prepared by machining the light metal board 2 into the form of a Fresnel lens.

Figure 7:
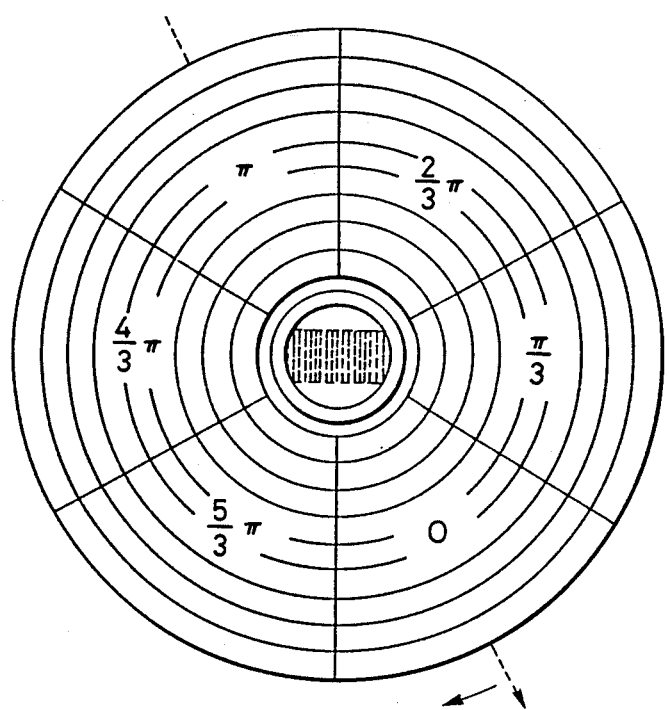
FIG. 7, FIGS. 9A and 9B, and FIGS. 10A, 10B and 10C are top plan views showing the phase controls of the respective probes.

The overall construction of the system will be described with reference to FIG. 3. A main controller 10 feeds to a transmitting phase controller 11 a signal which determines the radius of an annular focal zone (A1, A2 of FIG. 2) to be formed, the distance of the focal plane from the probe and the modulation mode along the annulus. In the transmission phase controller 11, the drive signals are provided for the respective elements of the transducer 1, as will be later described in detail, are operated in accordance with the signals from the main controller 10 until they are transferred as load data to m-bit counters 8. These m-bit counters 8 are made operative using load data as their initial values, which affects the phase or timing of their output signals, and they count clocks of a frequency of $2^m \cdot f_0$ from the main controller 10. The m-bit counters 8 output their highest-bit signals as the irradiating transmission phase. Phase-controlled signals having the frequency $f_0$ to transmission amplifiers 9. These having transmission amplifiers 9 amplify those transmission phase-controlled signals to have amplitudes according to the signal from the main controller 10 to drive through separate circuits connected to each of the nine elements of sector of transducer 1 as illustrated in FIGS. 4 and 6. A separate transmitting controller 11, including m-bit counters 8 and transmission amplifiers 9, although not shown, is provided for similarly controlling the drive signals to the elements in the other five sectors of the transducer 1 of the embodiments illustrated in FIG. 4 and 6. As a result, the drive phases of the respective elements are individually controlled so that the initial phases of driving signals of the respective transducer elements may have a phase distribution which is rotated 360 degrees for one rotation in the circumferential direction on a face of the transducer as illustrated in FIG. 7. As will be described below in connection with FIGS. 13A and 13B, the initial phase of driving signals of the respective transducer elements may have a phase distribution which is rotated two, three or more times for one rotation in the circumferential direction on a face of the transducer 1 and thus vary the size of the focal zone.

Here, an example of the drive phases necessary for generating the sound field of the type shown in FIG. 2 will be described in the following. It is assumed here, as shown in FIG. 2: that the rotationally symmetric axis of the probe is designated by a Z-axis; that cylindrical coordinates using the intersection between the probe and the Z-axis as an origin are designated at $(Z, r, \Theta)$; that the coordinates of the center of a k-th transducer element are designated at $(Z_k, r_k, \Theta_k$; and that the coordinates of the annulus of the annular focal zone are designated by $Z=Z_F$ and $r=r_F$. With these assumptions, the drive phase $\phi_k$ (wherein k designates a natural number) to be given to each element is generally expressed by the following equation:

$$\phi_k(Z_k, r_k, \Theta_k, t) = \alpha(Z_k, r_k) + \beta(\Theta_k) + \omega_0 \cdot t \quad (3).$$

wherein $\omega_0$ designates the angular frequency of the ultrasound waves to be transmitted.

In the righthand side of the equation for giving the drive phase, the function $\alpha$ of $(Z_k, r_k)$ provides factors for determining the depth $Z_F$ of the focal plane and the radius $r_F$ of the annular focal zone. Two methods exist for calculating the function o. One method is to determine the drive phase of each element such that the sound waves may converge at the position $(Z_F, r_F)$ of the annulus in the section of the probe. According to this method, the function $\alpha$ is given by the following equation:

$$\alpha(Z_k, r_k) = 2\pi/\lambda_0 [\sqrt{(Z_k - Z_F)^2 + (r_k - r_F)^2} - Z_F]. \quad (4)$$

Another method is to form the annular focal zone by giving the driving phases which are calculated to locate the focal point at $(Z_F, 0)$, with further modulation by changing the drive polarity of each element. In order to consider what drive polarity is to be given, it is convenient to invert the time axis in the propagation of the sound waves. Since the sound wave A by the annular sound source having the radius $r_F$ is expressed by the following equation:

$$A \propto J_0\left(\frac{2\pi r_F}{\lambda_0}\sin\theta\right) \approx J_0\left(\frac{2\pi r_F}{\lambda_0}\theta\right) \quad (5)$$

(wherein $J_0$ designates the 0-th order Bessel's function; and $\Theta$ designates an azimuth angle), more specifically, the sound field is generally proportional to $J_0$ $(2\pi r_F/\lambda_0 \cdot r_k/Z_F)$ on the circumference of the radius $r_k$ on the face of the probe spaced at the distance $Z_F$. Therefore, the annular focal zone of the radius $r_F$ at the distance $Z_F$ from the probe can be formed by giving the following drive phase to each element. If the h-th zero point of the 0-th order Bessel's function is designated at ah and if the following equation holds:

$$c = \frac{\lambda_0 Z_F}{2\pi r_F} \quad (6)$$

(i) $r_k < a_1 r_C$ or $a_2 h r_C < r_k < a_{2h+1} r_C$: (7)

$$\alpha(Z_k, r_k) = \frac{2\pi}{\lambda_0}[\sqrt{(Z_k - Z_F)^2 + r_k^2} - Z_F]$$

(ii) $a_{2h-1} r_C < r_k < a_{2h} r_C$: (8)

$$\alpha(Z_k, r_k) = \frac{2\pi}{\lambda_0}[\sqrt{(Z_k - Z_F)^2 + r_k^2} - Z_F] + \pi$$

(wherein h designates a natural number). Incidentally, if the probe has a constant radius of curvature R, as shown in FIG. 4, the following equation holds in the equations (4), (7) and (8):

$$Z_k^2 - 2Rk + r_k^2 = 0 \quad (9)$$

If, on the other hand, the probe has an infinite radius of curvature, as shown in FIG. 8, the following equation holds:

$$Z_k = 0 \quad (10)$$

In accordance with either method, the depth $Z_F$ of the focal plane and the radius $r_F$ of the annular focal zone are determined by the term $\alpha$ of the phase according to the radial position $r_k$ of the oscillating elements.

On the righthand side of the equation for giving the drive phase, the term $\beta$ of the function of $\Theta_k$ is calculated in the following manner. In the case of the dipolar annular focal zone of FIG. 2, the function $\beta$ is given by the following equation:

$$\beta(\theta_k) = \theta_k \quad (11)$$

In other words, the phase of the drive signal of each element is rotated 360 degrees for one rotation in the circumferential direction on the face of the initial probe. In the probe of FIG. 4 or 6, the distribution of the phase of the drive signal 2 each element may have a pattern as shown in FIG. 7. On the other hand, in the embodiment of FIG. 8 the distribution of the phase of the drive signal to each element may have a pattern as the shape shown in FIG. 9. In the present embodiment, the phase distribution is rotated with lapse of time while the phase difference between the elements lying along a radius is held constant. Since the equi-phase plane of the sound pressure is rotated in the direction of the arrow, as shown in FIG. 2, on the focal plane P by that rotation of the phase distribution, the energy of the sound waves is uniformly distributed in an annular form as a certain time elapses to thus be modulated along the annulus. Because the energy A1 is positive and the energy A2 is negative, the integration of sound pressure on the focal plane P may substantially equal zero and the acoustic energy necessary for forming annular focal zones A1 and A2 on the focal plane P can be concentrated without forming a secondary focal point B all as explained above.

Although the description far is directed to the case in which the a dipolar annular focal zone is formed, the polar number can be increased to form a focal zone of 2n poles. In this case, the term $\beta(\Theta_k)$ of the equation (3) is given by the following equation:

$$\beta(\theta_k) = n\theta_k \quad (12)$$

Thus, the drive phase $\phi_k$ obtained from the equation (3) is quantitized at a unit of $2\pi/2^m$ so that its lower m bits are outputted from the transmitting phase controller 11 to produce the load data of the m-bit counters 8. As a result, each element is driven by the phase which is designated at $\phi_k$.

In the case of the example in FIG. 7, the number of driving amplifiers 9 in FIG. 3 can be decreased by half by changing the piezoelectric polarity of transducer elements 1. For instance, positive polarity is given to '0', $\pi/3$', and '$2\pi/3$' elements in FIG. 7, negative polarity is given to others, and point symmetric pairs of elements are electrically combined by pairs.

The embodiment of FIG. 3 is equipped with an irradiation monitoring imaging means in addition to the irradiating transmitting phase means, as will be described in the following. In FIG. 3, reference numeral 6 designates the imaging auxiliary probe, and numeral 7 designates the motor for rotating the probe 6 on the Z-axis so that a plurality of ultrasound echo tomograms necessary for positioning the irradiation target can be formed. Each of the elements of the auxiliary probe 6 is connected through a transmitting and receiving amplifier 13 with a transmitting controller 12 and a receiving beam former 14. The drive signals having their phases controlled for each element by the transmitting controller 12 are repeatedly applied through the transmitting and receiving amplifiers 13. As a result, an ultrasound beam for the known linear scanning imaging or sector scanning imaging is repeatedly emitted from the probe 6 into a certain section in the object. This ultrasound beam has a frequency equal to the resonance frequency of the auxiliary probe 6.

Both the echo signals generated due to discontinuity of the acoustic impedance in the object and the harmonics signals generated due to the acoustical nonlinear effect by the irradiating ultrasound waves are received by the respective elements of the imaging auxiliary probe 6, amplified by the transmitting and receiving amplifiers 13, and focused by the receiving beam former 14. As a result, there are generated signals which are indicative of the time changes in the intensity of the reflected signals or the harmonics signals based on the received beam which is sequentially scanned for the known linear scanning or sector scanning imaging. These signals are fed through an imaging circuit 15 to a display unit 16 so that the generated positions and the ultrasound intensities of the echo signals or the harmonics signals are displayed through the imaging circuit 15 in the display frame of the display unit 16. The receiving beam former 14 is equipped with not only electronically scanning means and electronically focusing means but also a band-pass filter so that its center frequency is registered to the imaging ultrasound frequency, which is more than twice as high as the irradiating ultrasound frequency. This makes the ultrasonic imaging operation possible without any interference even during the ultrasonic irradiation. The display frame has a function to store and display two images, as designated at 17-1 and 17-2, so as to make it convenient to position the irradiation target. Therefore, the operator operates the auxiliary probe by means of the motor 7 so that the tomograms taken in two arbitrary directions can be monitored by means of the display unit 16. Moreover, the monitor unit of the present embodiment superposes the tomographs of the object to display the focal zone of the ultrasound beam emitted from the oscillator 1 in the form of markers (as designated at 18-1 and 18-2 in FIG. 3). The imaging circuit 15 generates the marker signals indicating the section of the focal zone by using the signals indicating the depth and radius of the annular focal zone from the main controller 10 and feeds them to the display unit 16. On the other hand, numerals 19-1 and 19-2 designate markers indicating the positions of the center axis of the probe.

By this imaging means, the following kinds of irradiation monitors can be accomplished:

(1) The irradiation target is identified and positioned by the ultrasonic imaging;

(2) The movement of the irradiation target is detected to move the irradiation zone in accordance with the movement detected;

(3) The change in the acoustic impedance and in the sound velocity due to th temperature rise of the irradiation zone is observed by measuring the intensity and the of echo signal reflected from the irradiation zone;

(4) The harmonics waves generated in the irradiation zone by the acoustical non-linear effect are observed; and (5) The harmonics waves generated in the so-called "hot spot" other than the target zone are monitored The monitor (1) has an advantage that it is reluctant to be influenced by the refraction even if a sound velocity distribution is present in the human body, because the target is positioned by the similar ultrasound waves as the irradiated waves and not by other means such as X-rays. The monitor (2) makes use of the high speed of the ultrasond pulse echo imaging ans is suited especially for electronic scanning type ultrasonic imaging means. Since the three-dimensional detection of the movement of the irradiation target is required, the scanning has to be made with the ultrasond beam three dimensionally by using the two-dimensional array type probe or by combining the electronic scanning and the mechanical scanning. The monitor (3) observes the change in the reflected echo intensity, which is caused by the change of the acoustic impedance or the product of the sound velocity and the specific gravity both changing as a result that the temperature of a substance in the irradiated zone is raised by the ultrasound wave absorption. The monitor (3) also observe the change in the reflected echo phase, which is caused by the change in sound velocity.

Thus, the monitor (3) is effective especially for the monitor of the ultrasound heating. Identally, this method partly disclosed in detail on p. i. 788 of "American Acoustics Report", Vol 15, No. 11 and in the U.S. Pat. No. 4,566,459. by the nonlinear acoustic parameter A/B of a substance or the cavitation in the irradiation zone, there are generated the harmonics components of the irradiating ultrasound waves, which are observed according to the monitor (4) to provide information of the intensity and action of the ultrasound waves in the generation zone. If waves having a relatively high reflection intensity are present in the irradiation target medium of the ultrasound waves, standing waves may be produced in the irradiation target medium to cause the so-called "hot spot" in other than the irradiation target zone. This irradiation zone unintended will be seriously dangerous especially in the application of medical treatment so that it has to be avoided by strictly monitoring it. The item (5) is intended to monitor the hot spot by observing the harmonics waves which are generated by the nonlinear acoustic effect.

In order to effect the items (4) and (5) among the aforementioned five kinds of monitors, it is necessary to stop the operation of the transmitting controller 12 thereby to detect only the harmonics waves which are generated as a result of the irradiation of the sound waves using the probe 1. On the other hand, if a color display unit is used as the display unit 16 and if the imaging circuit 15 is caused to generate display signals of different colors in case the amplitude of the harmonics waves detected exceeds a predetermined allowable limit, it is more preferable to call the attention of the operator.

In the embodiment thus far described, the depth $Z_F$ and radius $r_F$ of the annular focal zone are determined by the phase adjustment (i.e., the term of $\alpha(Z_k, r_k)$ of the equation (3)) according to the radial position $r_k$ of the drive signal of the divided transducer 1. However, the radius $r_F$ can also be controlled by the polar number (i.e., 2n of the equation (12)) of the rotations of the drive signals along the circumferential position of the oscillator. Therefore, the term of $\alpha(Z_k, r_k)$ of the equation (3) may be determined by the following equation in place of the equation (4):

$$\alpha(Z_k, r_k) = 2\pi/\lambda_0 (\sqrt{(Z_k - Z_F)^2 + r_k^2} - Z_F) \quad (13)$$

The above equation (13) implies that the drive phase according to the radial position $r_k$ of the elements of the probe 1 is so calculated that it is focused in the center position of the focal plane of the desired depth $Z_F$.

In case the probe of FIG. 8 is used, on the other hand, the drive phase may be inverted into a stripe form at the position of the two-dimensional array in place of the adjustment of the drive phase according to the element position of the probe in the circumferential direction, as expressed by the equation (11). At this time, the drive phase $\phi_k$ element located at $(Z_k, r_k, \Theta_k)$ is expressed by the following equation:

$$\phi_k(Z_k, r_k, \theta_k) = \frac{2\pi}{\lambda_0} [\sqrt{(Z_k - Z_F)^2 + r_k^2} - Z_F] + \gamma(Z_k, r_k, \theta_k) + \omega_0 t \quad (13)$$

Figure 10A:
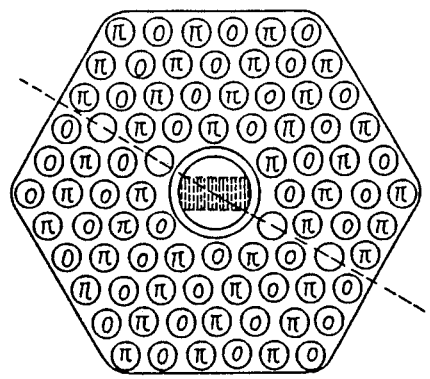
Figure 10B:
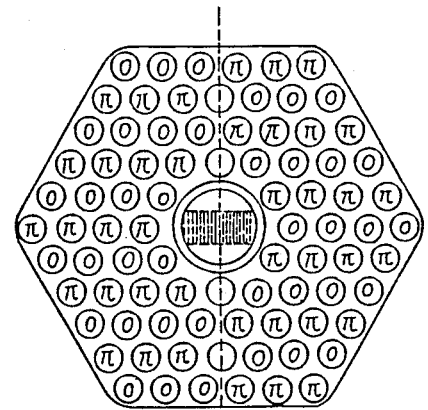
Figure 10C:
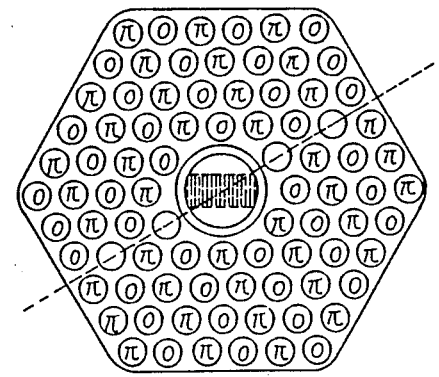
Figure 11A:
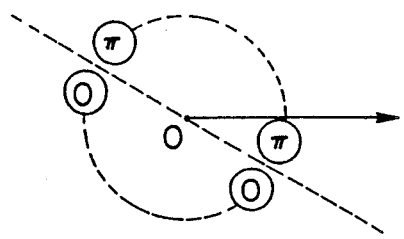
FIGS. 11A, 11B and 11C are schematic diagrams obtained by the phase controls of FIGS. 10A, 10B and 10C.
Figure 11B:
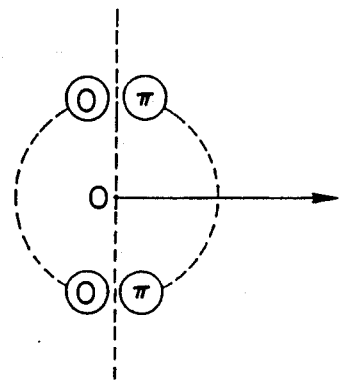
Figure 11C:
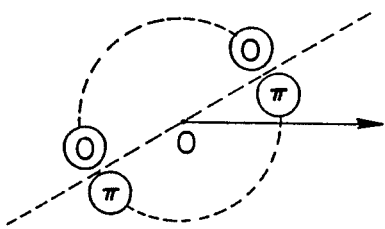

Here, the phase denoted by $\gamma$ is shown in FIGS. 10A, 10B and 10C, for example. By thus controlling the drive phase, a plurality of spots in different polarities can be simultaneously formed on the focal plane P, respectively, as shown in FIGS. 11A, 11B and 11C. By the irradiation while switching the modes of FIGS. 11A, 11B and 11C, the ultrasound wave energy can also be distributed in an annular form on a time average. By using specified one of modes of FIGS. 11A, 11B and 11C, moreover, it is possible to form an ultrasound wave energy distribution which is suitable for a rotationally asymmetric irradiation target zone.

Figure 1:
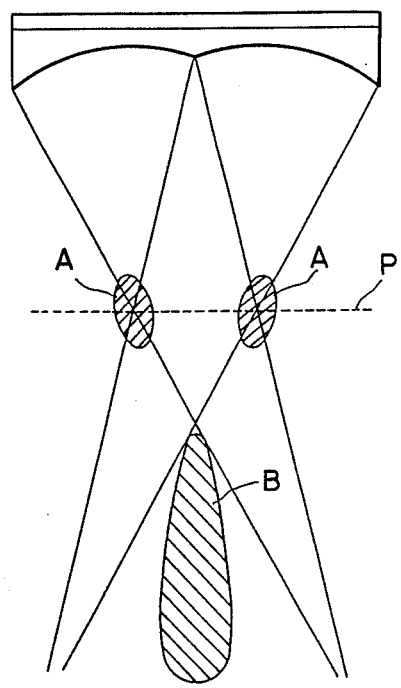
FIG. 1 is a sectional view showing the probe and its focal zone of the prior art.
Figure 9A:
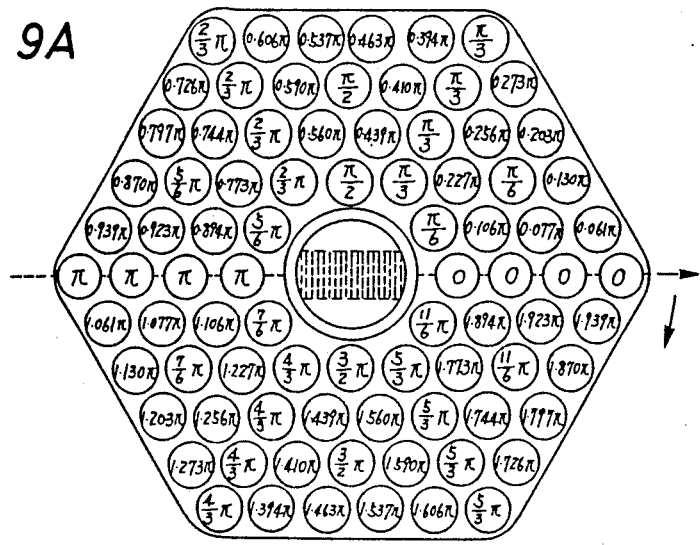
Figure 9B:
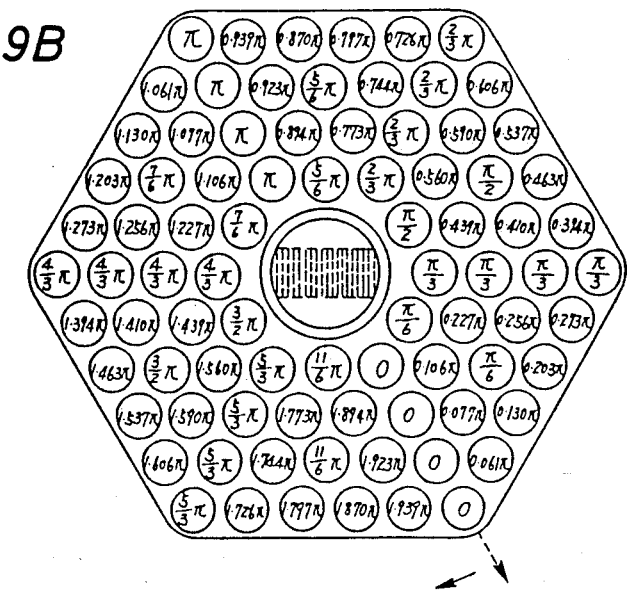

The feature shared commonly among the examples of FIGS. 7, 9 and 10 showing the distributions of the phase of the sound pressures on the faces of the transducer elements of the two dimensional array type ultrasound transducer is that the drive phases of the respective elements are so controlled that the integral of their value can always be substantially neglected as compared with the integral of their absolute value. This control provides on effective method for forming such a sound field that the integral of sound pressure can be substantially neglected in comparison with the integral of the absolute value of the sound pressure on the focal plane. As a result, the annular focal zone can be formed without forming the secondary focal zone B shown in FIG. 1.

Figure 12A:
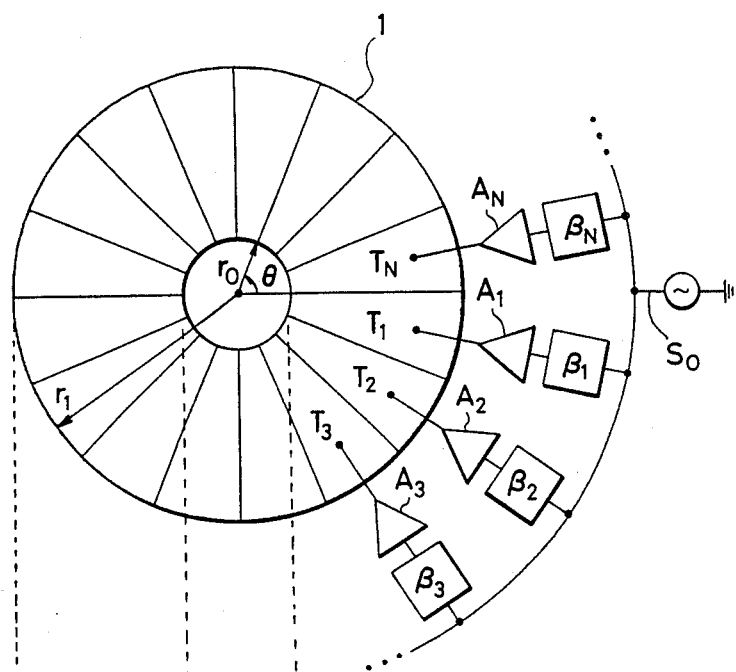
FIGS. 12A and 12B are a top plan view and a sectional view showing a probe according to another embodiment of the present invention.
Figure 12B:
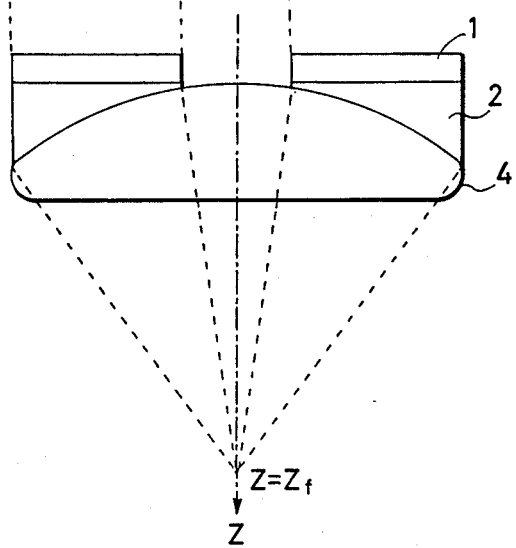

FIGS. 12A and 12B show the structure of the probe according to still another embodiment of the present invention. This embodiment has a fixed focal point using an acoustic lens in place of the control of the drive phase using the term $\beta(Z_k, r_k)$ of the equation (3) and forms the annular focal zone. The transducer 1 for the sound wavetransmission is divided into a plurality of annular piezoelectric elements $T_1, T_2, —,$ and $T_N$ having an internal radius $r_0$ and an external radius $r_1$. These elements are attached to the back of the acoustic lens 2 having the focal length $Z_F$. Reference numeral 4 designates a water bag.

If the polar coordinates $(r, \Theta)$ are taken in the array form of the transducer elements and if the angular coordinates of the i-th element are designated at $\Theta_i$ whereas the amplitude of the drive signal is designated at $A(\Theta_k)$, then the drive signal is controlled to satisfy the following equation:

$$A(\Theta_k) = A_0 e^{j[n(\Theta_k + \beta_1(\Theta_k)) - \omega_0 t]} \quad (14).$$

More specifically, the control is made such that the phase of the drive signal proceeds on the annular transducer in the circumferential direction at the anguler velocity $\omega_p$ given by the following equation:

$$\omega_p = \omega_0 / n \cdot (1 + \beta_1'(\Theta_k)) \quad (15)$$

Here: $\omega_0$ designates the angular velocity of the ultrasound waves; n designates the number of phase rotation per rotation in the circumferential direction; $\beta_1'(\Theta_k)$ designates a function expressing the azimuth modulation of the phase angular velocity; and $A_0$ designates a constant.

For simplicity, the sound field B on the focal plane in the absence of the modulation $\beta_1'(\Theta_k)$ is calculated. If the polar coordinates on the focal plane are designated at $(R, \bigoplus)$, if the wave number of the ultrasound waves is designated at k, and if the following equation holds:

$$K_F = kR/Z_F \quad (16),$$

then the following equation is obtained:

$$B = \int_{r_0}^{r_1} \int_0^{2\pi} A(\theta) e^{jK_F r \cos(\theta - \bigoplus)} r d\theta dr = \quad (17)$$

$$A_0 e^{j[n(\bigoplus + \pi/2) - \omega t]} \int_{r_0}^{r_1} \int_0^{2\pi} e^{j(n\theta - K_F r \sin\theta)} d\theta dr =$$

$$A_0 e^{j[n(\bigoplus + \pi/2) - \omega t]} \int_{r_0}^{r_1} J_n(K_F r) 2\pi r d\theta.$$

If $r_2 = \frac{2}{3}(r_1^3 - r_0^3)/(r_1^2 - r_0^2)$, the equation (17) can be approximated into the following form:

$$B = A_0 e^{j[n(\bigoplus + \pi/2) - \omega t]} \cdot \pi(r_1^2 - r_0^2) J_n(k_F r_2) \quad (18)$$

In other words, the sound field B has a radial distribution with the form of an n-th order Bessel's function As a result, annular focal zones of different radii can be formed by changing the phase rotation number n.

Figure 13A:
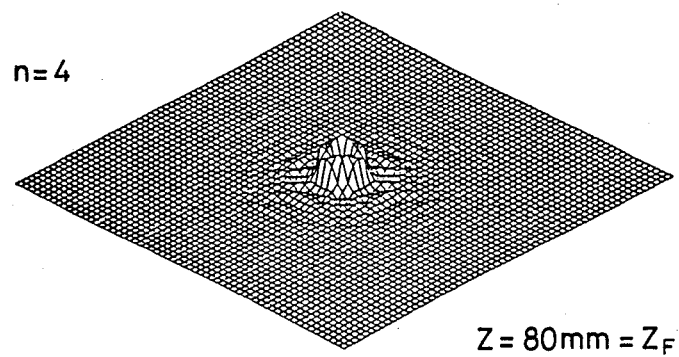
FIGS. 13A and 13B are schematic diagrams showing sound waves obtained by the probe of FIGS. 12A and 12B.
Figure 13B:
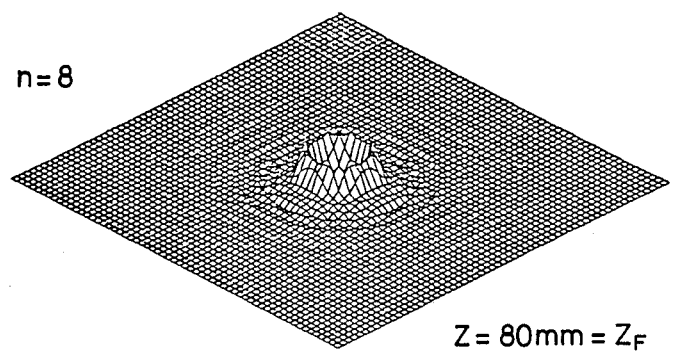

FIGS. 13A and 13B show the sound pressure distribution (in absolute values) of the sound field on a focal plane, which is established for an ultrasound frequency of 0.5 MHz, a transducer having an internal diameter of $r_0 = 20$ mm and an external diameter $r_1 = 60$ mm, a focal length of $Z_F = 80$ mm and a probe having an element number of $N = 64$, and when the phase rotation number n of the drive signal per one rotation is set at $n = 4$ and $n = 8$. It is found that the radius of the focal zone on the focal plane is substantially proportional to the phase rotation number n.

Furthermore, an elongated annular focal zone is formed by modulating the angular velocity p given by equation (15) using the modulation term $\beta_1(\Theta_k)$. For example, when the transducer in FIG. 12A and 12B is driven by the signal with $n = 8$ and $$\beta_1(\Theta_i) = 0.15 \sin 2\Theta, \quad (19)$$

an oval-shaped focal zone with an aspect ratio ·1.35 is formed on the focal plane.

Incidentally, the embodiment of FIG. 13 shows the case in which the acoustic lens is used for the geometrical focusing (i.e., to determine the focal length $Z_F$). However, the geometrical focusing can also be done by making the shape of the transducer elements concave.

In the predescribed embodiments, the shapes of the transducers were circular or regular polygonal. This invention can also be applied to transducers with other types of shapes such as elongated circles or elongate polygons.

The embodiments thus far described forms the focal zone and controls its diameter by using the probe having the two dimensional or radially divided array of elements and by rotating the phases of the driving signals in the circumferential direction. However, the formation of the annular focal zone and the control of the zone radius can also be realized by using an (annular array) probe composed of a number of multi-ring-shaped transducer elements.

Figure 14A:
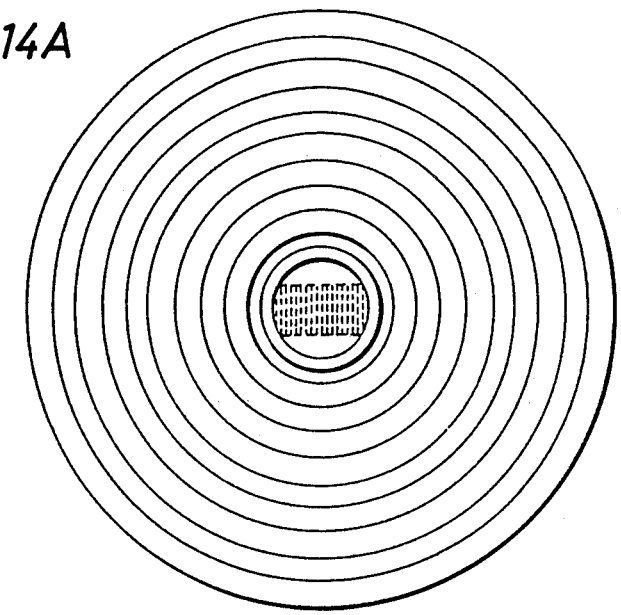
FIGS. 14A and 14B are a top plan view and a sectional view showing a probe according to still another embodiment of the present invention.
Figure 14B:
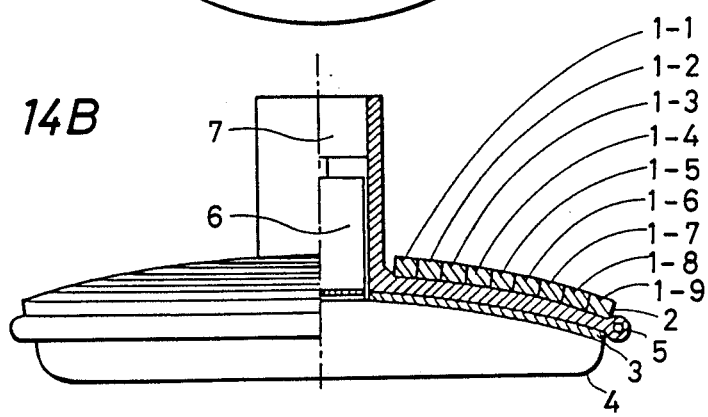

FIG. 14 shows this embodiment, in which reference numerals 1-1, 1-2, 1-3, —, and 1-9 designate transducer elements divided into a multiplicity of rings whereas the remaining numerals are the same as those of the embodiment of FIG. 4. If there are taken cylindrical coordinates having a rotationally symmetric axis of the probe located on the Z axis and an origin located at the center of the probe and if the coordinates of a k-th transducer element are $Z=Z_k$ and $r=r_k$ and the coordinates of the annulus of the central portion of an annular focal zone are $Z=Z_F$ and $r=r_F$, the phase $\phi_k$ of the drive signal to be fed to that k-th transducer element is given by the following equation:

$$\phi_K = \frac{2\pi}{\lambda_0} [\sqrt{(Z_K - Z_F)^2 + (r_K - r_F)^2} - Z_F] \quad (20)$$

Here $\lambda_0$ designates the wavelength of the irradiation ultrasound waves.

What is claimed is:

1. An ultrasonic irradiation system comprising:
a transducer having a generally circular contour and divided into a plurality of transducer elements which extend in a circumferential direction;
drive circuit means for providing said transducer elements with respective drive signals which all have the same frequency; and
control circuit means for controlling the phases of said drive signals so that initial phases of drive signals supplied to respective transducer elements have a phase distribution which is rotated "n times 360°" for one rotation in the circumferential direction on a face of said transducer where "n" is an integer greater than 0.

2. The ultrasonic irradiation system as defined in claim 1, wherein "n" is the integer one.

3. The ultrasonic irradiation system as defined in claim 1, wherein "n" is an integer greater than one.

4. An ultrasonic irradiation system as defined in claim 1, further comprising an acoustic lens at front surfaces of said transducer elements, said lens having a predetermined focal point.

5. An ultrasonic irradiation system as defined in claim 1, wherein the transducer elements are mounted on a support board and said support board has a concave shape to focus ultrasonic irradiation energy produced by said transducer.

6. The ultrasonic irradiation system according to claim 1, further comprising:
an array type of monitoring probe disposed at the center of said transducer;
rotation means mechanically coupled to said monitoring probe for rotating the array direction of said monitoring probe; and
means responsive to sound waves for producing an image of an object by electronic scanning by said monitoring probe.

7. An ultrasonic irradiation system comprising:
a transducer having a generally circular contour and divided into a plurality of transducer elements in a circumferential direction;
a plurality of drive circuit means for providing each of said transducer elements with respective drive signals which all have the same frequency; and
control circuit means connected with the drive circuits and transducer elements for controlling the phase of each of said drive signals, including means for forming an annular zone of energy concentration on a focal plane without forming a second zone of energy concentration on a second focal plane by supplying to said transducer elements drive signals that have an initial phase distribution which is rotated "n times 360°" for one rotation in the circumferential direction on a face of the transducer where "n" is an integer greater than 0.

8. An ultrasonic irradiation system comprising:
a transducer having a generally circular contour and divided into a plurality of transducer elements in both circumferential and radial directions;
drive circuit means for providing said transducer elements with respective drive signals which all have a same frequency; and
control circuit means for controlling the phases of said drive signals so that initial phases of driving signals of respective transducer elements have a phase distribution, said phase distribution including phase differences along radial directions on a face of said transducer so that ultrasonic waves irradiated from said transducer elements for an annular focal zone and further including "n times 360°" phase rotations for one rotation in the circumferential direction on said face of said transducer where "n" is an integer greater than 0.

* * * * *